(12) United States Patent
Burke et al.

(10) Patent No.: US 6,764,472 B1
(45) Date of Patent: Jul. 20, 2004

(54) IMPLANTABLE REFILLABLE INFUSION DEVICE

(75) Inventors: Paul F. Burke, Bellingham, MA (US); Kenneth A. Fine, Sharon, MA (US)

(73) Assignee: Bard Access Systems, Inc., Salt Lake City, UT (US)

(*) Notice: Subject to any disclaimer, the term of this patent is extended or adjusted under 35 U.S.C. 154(b) by 0 days.

(21) Appl. No.: 09/481,298

(22) Filed: Jan. 11, 2000

(51) Int. Cl.$^7$ ............................................. A61M 31/00
(52) U.S. Cl. ................................................. 604/288.04
(58) Field of Search .................... 604/890.1–892.1, 604/82–83, 85–86, 93.01, 131–134, 200–205, 212, 288.01–288.04

(56) References Cited

U.S. PATENT DOCUMENTS

| | | | |
|---|---|---|---|
| 3,682,315 A | 8/1972 | Haller | |
| 3,731,681 A | 5/1973 | Blackshear et al. | |
| 3,840,099 A | 10/1974 | Michaels et al. | 128/260 |
| 3,896,806 A | 7/1975 | Wichterle | |
| 3,951,147 A | 4/1976 | Tucker et al. | 128/260 |
| 3,971,376 A | 7/1976 | Wichterle | |
| 4,146,029 A | 3/1979 | Ellinwood, Jr. | |
| 4,193,397 A | 3/1980 | Tucker et al. | |
| 4,221,219 A | 9/1980 | Tucker | |
| 4,258,711 A | 3/1981 | Tucker et al. | |
| 4,286,584 A | 9/1981 | Sampson et al. | |
| 4,299,220 A | 11/1981 | Dorman | |
| 4,360,019 A | 11/1982 | Portner et al. | |
| 4,368,737 A | 1/1983 | Ash | |
| 4,373,527 A | 2/1983 | Fischell | |
| 4,417,888 A | 11/1983 | Cosentino et al. | |
| 4,447,237 A | 5/1984 | Frisch et al. | |
| 4,464,178 A | 8/1984 | Dalton | |
| 4,490,137 A | 12/1984 | Moukheibir | |
| 4,496,343 A | 1/1985 | Prosl et al. | |
| 4,525,165 A | 6/1985 | Fischell | |
| 4,543,088 A | 9/1985 | Bootman et al. | |
| 4,552,561 A | 11/1985 | Eckenhoff et al. | |
| 4,573,994 A | 3/1986 | Fischell et al. | |
| 4,576,211 A | 3/1986 | Valentini et al. | |
| 4,588,394 A | 5/1986 | Schulte et al. | |
| 4,604,090 A | 8/1986 | Reinicke | |
| 4,619,652 A | 10/1986 | Eckenhoff et al. | |
| 4,655,765 A | 4/1987 | Swift | |
| 4,673,391 A | 6/1987 | Kondo et al. | |
| 4,687,468 A | 8/1987 | Gianturco | |
| 4,692,146 A | 9/1987 | Hilger | |
| 4,692,147 A | 9/1987 | Duggan | |
| 4,695,273 A | 9/1987 | Brown | |

(List continued on next page.)

FOREIGN PATENT DOCUMENTS

| DE | 28 05 354 A1 | 2/1978 |
|---|---|---|
| EP | 0 335 671 A1 | 10/1989 |
| EP | 0 858 814 A1 | 1/1998 |
| WO | WO 80/02377 A1 | 11/1980 |

*Primary Examiner*—LoAn H. Thanh
(74) *Attorney, Agent, or Firm*—Wolf, Greenfield & Sacks, P.C.

(57) ABSTRACT

An implantable infusion device includes a lightweight, inert housing which contains an infusate for administration to a patient, and an enclosed, gas-impermeable variable volume chamber which contains a pressure source, such as propellant, mechanical spring, or the like. The variable volume chamber may be in the form of a rigid-walled expandable bellows structure or a nonstretchable flexible bag and is attached to the housing so as not to obstruct the entry port for introduction of infusate. The infusate is delivered from the device via a catheter in response to expansion of the variable volume chamber against the volume of infusate in the housing. A separate bolus injection port is provided which allows infusate to be safely introduced directly into the catheter and overrides the controlled pressure-driven delivery. The lightweight housing may include integrally formed needle stops and suture fastening loops.

39 Claims, 4 Drawing Sheets

U.S. PATENT DOCUMENTS

| | | |
|---|---|---|
| 4,710,174 A | 12/1987 | Moden et al. |
| 4,714,462 A | 12/1987 | DiDomenico |
| 4,718,893 A | 1/1988 | Dorman et al. |
| 4,731,051 A | 3/1988 | Fischell |
| 4,760,837 A | 8/1988 | Petit |
| 4,781,680 A | 11/1988 | Redmond et al. |
| 4,784,645 A | 11/1988 | Fischell |
| 4,784,646 A | 11/1988 | Feingold |
| 4,810,246 A | 3/1989 | Frisch et al. |
| 4,820,273 A | 4/1989 | Reinicke |
| 4,826,487 A | 5/1989 | Winter |
| 4,832,054 A | 5/1989 | Bark |
| 4,834,713 A | 5/1989 | Suthanthiran |
| 4,857,053 A | 8/1989 | Dalton |
| 4,871,351 A | 10/1989 | Feingold |
| 4,886,501 A | 12/1989 | Johnston et al. |
| 4,892,518 A | 1/1990 | Cupp et al. |
| 4,904,241 A | 2/1990 | Bark |
| 4,922,926 A | 5/1990 | Hirschberg et al. |
| 4,931,050 A | 6/1990 | Idriss |
| 4,955,861 A | 9/1990 | Enegren et al. |
| 4,969,873 A | 11/1990 | Steinbach et al. |
| 5,006,115 A | 4/1991 | McDonald |
| 5,009,644 A | 4/1991 | McDonald |
| 5,045,064 A | 9/1991 | Idriss .................. 604/132 |
| 5,053,031 A | 10/1991 | Borsanyi |
| 5,061,242 A | 10/1991 | Sampson |
| 5,085,656 A | 2/1992 | Polaschegg |
| 5,088,983 A | 2/1992 | Burke |
| 5,135,497 A | 8/1992 | Hessel et al. |
| 5,135,502 A | 8/1992 | Koenig, Jr. et al. |
| 5,137,529 A | 8/1992 | Watson et al. |
| 5,167,625 A | 12/1992 | Jacobsen et al. |
| 5,167,633 A | 12/1992 | Mann et al. ............. 604/141 |
| 5,167,638 A | 12/1992 | Felix et al. |
| 5,176,653 A | 1/1993 | Metais |
| 5,180,365 A | 1/1993 | Ensminger et al. |
| 5,201,728 A | 4/1993 | Giampapa |
| 5,207,644 A | 5/1993 | Strecker |
| 5,248,301 A | 9/1993 | Koenig, Jr. et al. |
| 5,281,210 A | 1/1994 | Burke et al. |
| 5,318,540 A | 6/1994 | Athayde et al. |
| 5,328,465 A | 7/1994 | Kratoska et al. |
| 5,368,571 A | 11/1994 | Horres, Jr. |
| 5,395,324 A | 3/1995 | Hinrichs et al. .............. 604/86 |
| 5,443,450 A | 8/1995 | Kratoska et al. |
| 5,445,616 A | 8/1995 | Kratoska et al. |
| 5,507,737 A | 4/1996 | Palmskog |
| 5,514,103 A | 5/1996 | Srisathapat et al. ......... 604/141 |
| 5,527,277 A | 6/1996 | Ensminger et al. |
| 5,527,307 A | 6/1996 | Srisathapat et al. |
| 5,556,381 A | 9/1996 | Ensminger et al. |
| 5,558,640 A | 9/1996 | Pfeiler et al. |
| 5,575,770 A * | 11/1996 | Melsky et al. |
| 5,607,418 A | 3/1997 | Arzbaecher |
| 5,637,088 A | 6/1997 | Wenner et al. |
| 5,695,490 A | 12/1997 | Flaherty et al. |
| 5,722,957 A | 3/1998 | Steinbach |
| 5,752,930 A | 5/1998 | Rise et al. |
| 5,769,823 A | 6/1998 | Otto .......................... 604/141 |
| 5,785,681 A | 7/1998 | Indravudh |
| 5,814,019 A | 9/1998 | Steinbach et al. |
| 5,836,915 A | 11/1998 | Steinbach et al. |
| 5,897,528 A | 4/1999 | Schultz |
| 5,908,414 A | 6/1999 | Otto et al. ................ 604/891.1 |
| 5,925,017 A | 7/1999 | Kriesel et al. .............. 604/132 |
| 5,925,030 A | 7/1999 | Gross et al. ............. 604/890.1 |
| 5,928,195 A | 7/1999 | Malamud et al. |
| 5,957,890 A | 9/1999 | Mann et al. ................ 604/131 |
| 5,976,109 A | 11/1999 | Heruth |
| 6,039,712 A | 3/2000 | Fogarty et al. |
| 6,048,328 A | 4/2000 | Haller et al. |
| 6,053,891 A | 4/2000 | DeCampli |
| 6,152,898 A | 11/2000 | Olsen |
| 6,168,575 B1 | 1/2001 | Soltanpour |
| 6,228,050 B1 | 5/2001 | Olsen et al. |
| 6,238,367 B1 | 5/2001 | Christiansen et al. |
| 6,280,416 B1 | 8/2001 | Van Antwerp et al. |
| 6,283,943 B1 | 9/2001 | Dy et al. |
| 6,283,949 B1 | 9/2001 | Roorda |
| 6,485,464 B1 | 11/2002 | Christenson et al. |
| 6,572,583 B1 | 6/2003 | Olsen et al. |
| 6,589,198 B1 | 7/2003 | Soltanpour et al. |
| 6,645,176 B1 | 11/2003 | Christenson et al. |
| 2003/0082507 A1 | 5/2003 | Stypulkowski |
| 2003/0088236 A1 | 5/2003 | Johnson et al. |

\* cited by examiner

IMPLANTABLE REFILLABLE INFUSION DEVICE

TECHNICAL FIELD

The invention relates to implantable infusion devices for controllable in vivo delivery of drugs to a patient.

BACKGROUND OF THE INVENTION

Implantable infusion devices provide a patient with an in vivo source of a drug to be administered, in a device which permits controlled delivery of the drug over a predetermined time period. Certain drugs, such as, for example, chemotherapy drugs and opioids, may be most effective if administered at a constant dose rate, instead of at discrete intervals.

A typical infusion device or pump includes a hermetically sealed outer housing which holds a vapor pressure fluid or other means for exerting a compressive force on a compressible or flexible inner drug reservoir which communicates with a drug delivery port. Alternatively, the drug may be disposed in the outer housing, with a propellant disposed in the inner housing. When the outer housing is filled with the drug, the propellant in the inner housing is compressed and changes state from a vapor to a liquid, thereby recharging the driving mechanism of the device. In still other embodiments, the outer housing may be divided into two chambers separated by a liquid-impermeable diaphragm. One chamber contains the drug and includes a drug delivery port, and the other chamber contains a propellant or spring member for exerting a force against the diaphragm so as to expel the drug through the delivery port.

The infusion device must meet numerous requirements for safety and efficacy. For example, the housing material must not react with body fluids or with the drugs and propellants inside the housing. Further, the membrane or flexible barrier between the chambers must not leak and must be impermeable to gas-phase fluids so as to prevent contamination of the drug with the propellant. Since the device is designed for implantation into a patient, great care must be taken to prevent any leakage of either the drug or the propellant into the patient's body. In addition, the device is desirably as small and lightweight as possible so as to cause minimum invasive trauma, discomfort and disfigurement to the patient, yet sufficiently large to provide a useful therapeutic dosage of the drug being administered and minimize the frequency with which the device must be recharged. It is desirable to make the pump refillable so that it need not be surgically removed and replaced when the drug is depleted. However, refillability of the pump requires a port which is either outside of the skin or transcutaneously accessible without introducing infection or risking the release of an excessive and potentially harmful amount of the drug into the patient. Also, in those devices in which a propellant is contained within a flexible bag which expands and contracts in response to changes in the propellant pressure, it is necessary to ensure that introduction of the drug to the drug reservoir surrounding the propellant bag is not impeded by the presence and location of the bag in the reservoir and/or does not puncture or pinch the bag. Thus, it may be necessary to affix the propellant chamber or bag to the housing so as to avoid such problems. There is the additional problem of ensuring that the drug reservoir can be fully depleted and refilled, for optimum efficiency of the device.

Administration of a desired dosage of a drug over a period of time may require a controllable, constant flow of the drug from the device. However, as the drug is depleted from the reservoir, or if the force exerted on the drug reservoir cannot be controlled, a constant dose rate may be difficult to sustain.

U.S. Pat. No. 3,840,009 to Michaels et al. discloses a vapor pressure drug delivery device which has two chambers separated by a flexible wall or bladder. The outer chamber contains a drug to be administered to a patient, and the inner chamber contains a pressure fluid which expands to conform to the shape of the outer chamber, thereby enabling expulsion of substantially all of the drug within the outer chamber. The pressure fluid is maintained at a positive pressure at the temperature at which the device is used, so that no external power source is required.

U.S. Pat. No. 5,167,633 to Mann et al. discloses a medication infusion pump in which a constant pressure is exerted on a liquid medication to be administered. The pump includes a pressure reservoir in the form of a hollow enclosure with at least one flexible wall for containing a pressure fluid. The medication to be administered is outside of the pressure reservoir. The pressure fluid undergoes a phase change from a liquid to a vapor so as to expel the drug from the pump. The Mann et al. device is maintained at a negative pressure at the temperature of use to avoid leakage of medication from the pump into the patient.

U.S. Pat. No. 5,514,103 to Srisathapat et al. discloses a medication infusion pump including a drug reservoir and a pressure fluid reservoir which are separated by a movable wall or flexible bag. The pressure fluid reservoir includes a spacer therein to prevent contraction of the pressure fluid reservoir below a minimum volume which is slightly greater than the liquid phase volume of the pressure fluid, so that a portion of the pressure fluid always remains in a vapor phase. As a result, even when the drug reservoir is completely filled, the pressure fluid is not entirely in the liquid phase. Thus, additional energy to reinstate a vapor phase is not required.

U.S. Pat. No. 3,951,147 to Tucker et al. discloses a refillable implantable infusate pump in which a bellows containing a drug is contained within a housing which is filled with a pressure fluid or propellant. The Tucker et al. pump includes a filtering chamber to ensure removal of debris from the infusate drug prior to its delivery to the patient.

U.S. Pat. No. 5,045,064 to Idriss discloses a constant pressure implantable pump which employs shape-memory metal bands around a reservoir containing a fluid to be infused. The bands compress the reservoir containing the fluid to be infused, thereby eliminating the need for a propellant.

U.S. Pat. No. 5,395,324 to Hinrichs et al. discloses an infusion pump having a primary entry port leading to a drug reservoir, a separate bolus port leading to a bolus chamber, and means for ensuring that the bolus chamber is not inadvertently filled with the drug intended for the primary drug reservoir.

U.S. Pat. No. 5,769,823 to Otto discloses an implantable infusion pump which comprises a plastic housing, a bellows chamber enclosing a propellant, and two separate resilient plastic bags enclosing an infusate. The bags are surrounded by glycerin or the like which binds with any propellant passing through the bellows wall into the housing, thereby preventing passage of the propellant through the housing into the patient.

U.S. Pat. No. 5,575,770 to Melsky et al. discloses an implantable infusion pump having a valve-actuated bolus delivery chamber. Inadvertent administration of an overdose to the patient through the bolus delivery chamber is prevented by a design which requires the use of a side-access delivery needle, which is inserted through a pair of septa which are spaced apart to define a bolus chamber. The tip of the needle extends beyond the lower septum and depresses a lever to actuate the normally-closed valve. The side opening of the needle is disposed between the septa in the bolus chamber for delivery of the bolus dose to the bolus chamber. The design prevents erroneous dose delivery by requiring the simultaneous opening of the valve with delivery of the drug into the bolus using a side-access delivery needle.

It would be advantageous to provide an implantable infusion pump which is of simple construction and operation, made of lightweight materials, inexpensive to manufacture, efficient in the delivery of medicine, and easy to refill.

SUMMARY OF THE INVENTION

According to one aspect of the invention, there is provided an implantable infusion device, comprising a housing having an annular portion with an inner wall defining an interior region having a width dimension D and extending along a central axis, a bottom portion extending from the annular portion and spanning a first end of the interior region, and a top portion extending from the annular portion and spanning a second end of the interior region and being opposite the bottom portion, the interior region being substantially closed. The device further includes a closed fluid-impermeable hollow bellows extending from one of the top and bottom portions of the housing and defining a variable volume region therein and having a plurality of serially coupled annular members extending between top and bottom portions of the bellows. Junctions of the coupled annular members are coupled with flexures. The bellows has a maximum outer width dimension D' where D' is less than D. The portion of the housing from which the bellows extends includes a substantially planar annular peripheral portion disposed about a central portion. A pressure source is contained within the variable volume region of the bellows. The bellows is disposed within the interior region of the housing and rigidly coupled to the portion of the housing from which it extends. The annular members of the bellows are spaced apart from the annular portion of the housing. The housing includes a recharging fluid flow path from points external to the housing to a region adjacent to the central portion of the portion of the housing from which the bellows extends. The housing further defines a fluid exit flow path extending from the region between the bellows and the annular portion of the housing to points external to the housing.

The device further includes a pierceable, self-sealing septum disposed in the recharging fluid flow path and may further include a recharging fluid reservoir disposed along the recharging fluid flow path. The septum may be removable from the housing.

The device further includes at least one of a flow restrictor and a filter disposed along the fluid exit flow path.

In one embodiment, the housing is made of a gas-impermeable material, and the bellows which encloses the pressure source is made of a substantially rigid, gas-impermeable material. In a preferred embodiment, the bellows is hermetically sealed.

The pressure source comprises one or more of the group consisting of multiple-phase fluids, springs, shape memory metal alloys, Belville washers, and compressible materials. In one embodiment, a multiple-phase fluid propellant is present in at least one of a liquid phase and a gas phase within the variable volume region of the bellows as a function of ambient temperature. Conversion of the propellant fluid from a liquid phase to a gas phase increases the volume displaced by the bellows in the interior region of the housing, thereby exerting a force on a fluid external to the bellows in the housing so as to provide a substantially constant flow rate of the fluid through the fluid exit flow path.

In a preferred embodiment, the propellant is disposed in the variable volume region of the bellows at a pressure which is not less than atmospheric pressure at ambient temperature.

In one embodiment, the central portion of the bellows is offset from the plane of the annular peripheral portion of said bellows. A central region of the portion of the housing from which the bellows extends is correspondingly offset from the plane of the annular portion of the housing. The offset central region of the housing substantially nests within the offset central portion of the bellows.

In one embodiment, the housing and bellows are cylindrical.

The device can further include a separate bolus port in fluid communication with the fluid exit flow path. The bolus port can include a pair of septa which are spaced apart to define a bolus reservoir therebetween. A side-access delivery needle having an opening near the center of its length is required to delivery a bolus dose of the infusate to the bolus reservoir.

In one preferred embodiment, the bellows extends from the top portion of the housing. In another preferred embodiment, the bellows extends from the bottom portion of the housing.

According to another aspect of the invention, there is provided an implantable infusion device, comprising a housing having an annular portion with an inner wall defining an interior region having a width dimension D and extending along a central axis, a bottom portion extending from the annular portion and spanning a first end of the interior region, and a top portion extending from the annular portion and spanning a second end of the interior region, the top portion being opposite the bottom portion, the interior region being substantially closed. The device further includes a closed fluid-impermeable hollow bellows disposed about a variable volume region and having a top member, a bottom member, and a plurality of serially coupled annular members extending therebetween. Junctions of the coupled annular members are coupled with flexures. The bellows has a maximum outer width dimension D' where D' is less than D. At least one of the top and bottom members includes a substantially planar annular peripheral portion disposed about a central portion. A pressure source is contained within the variable volume region of the bellows, and the bellows is disposed within the interior region of the housing with one of the top and bottom members facing and rigidly coupled to a corresponding portion of the housing. The annular members of the bellows are spaced apart from the annular portion of the housing. The housing includes a recharging fluid flow path from points external to the housing to a region adjacent to the central portion of one of the top and bottom members of the bellows. The region of coupling between the housing and the bellows defines a fluid dispersal flow path from the region adjacent to the central portion of the coupled member of the bellows to a region between the annular members of the bellows and the annular portion of the housing. The housing further defines a fluid exit flow path extending from the region between the bellows and the annular portion of the housing to points external to the housing.

In one embodiment, a central portion of at least one of the top and bottom members of the bellows is offset from the plane of the annular peripheral portion of the top and bottom members of the bellows. A central region of the portion of the housing which is coupled to the bellows is correspondingly offset from the plane of the annular portion of the housing, so that the offset central region of the portion of the housing which is coupled to the bellows substantially nests within the central portion of the coupled portion of the bellows.

In one preferred embodiment, the bellows is coupled to the top portion of the housing. In another preferred embodiment, the bellows is coupled to the bottom portion of the housing.

According to still another aspect of the invention, there is provided a septum replacement kit for an enclosed device which is sealed with a septum, wherein the enclosed device defines a fluid reservoir, a fluid flow inlet and a fluid flow outlet. The kit comprises a compressible septum adapted to sealingly engage in the fluid flow inlet of the reservoir, and a septum installation tool adapted to compress the septum to a nominal insertion size, maintain the nominal insertion size of the septum prior to installation of the septum, and install the septum in the fluid flow inlet of the reservoir.

The septum installation tool preferably comprises a tubular member adapted for insertion into the fluid flow inlet of the reservoir, an opening in the tubular member for insertion and retention of the septum therein, and a plunger member disposable in the tubular member for expulsion of the septum from the tubular member. Insertion of the septum into the tubular member compresses the septum. Expulsion of the septum from the tubular member into the fluid inlet reservoir permits the septum to expand to fill in and seal the fluid inlet reservoir.

The septum is preferably made of a pierceable, self-sealing elastomeric or rubber-like material.

These and other objects and advantages of the invention will in part be obvious and will in part appear hereinafter. The invention accordingly comprises the apparatus possessing the construction, combination of elements and arrangement of parts which are exemplified in the following detailed disclosure, the scope of which will be indicated in the claims.

BRIEF DESCRIPTION OF THE DRAWINGS

For a fuller understanding of the nature and objects of the present invention, reference should be made to the following detailed description taken in connection with the accompanying drawings, in which.

Like features in the drawings are indicated with like numerals.

DETAILED DESCRIPTION OF THE DRAWINGS

Figure 1:
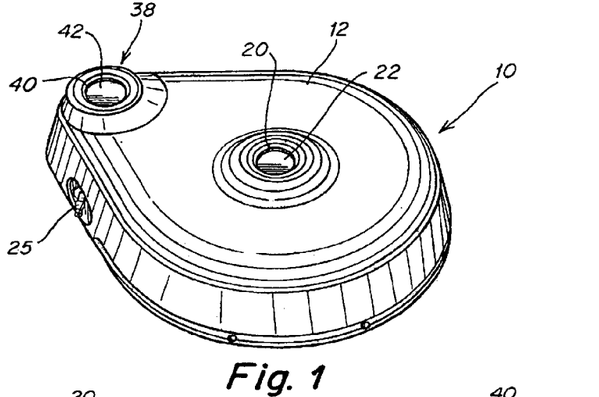
FIG. 1 is a perspective view of an infusion device according to the invention.
Figure 3:
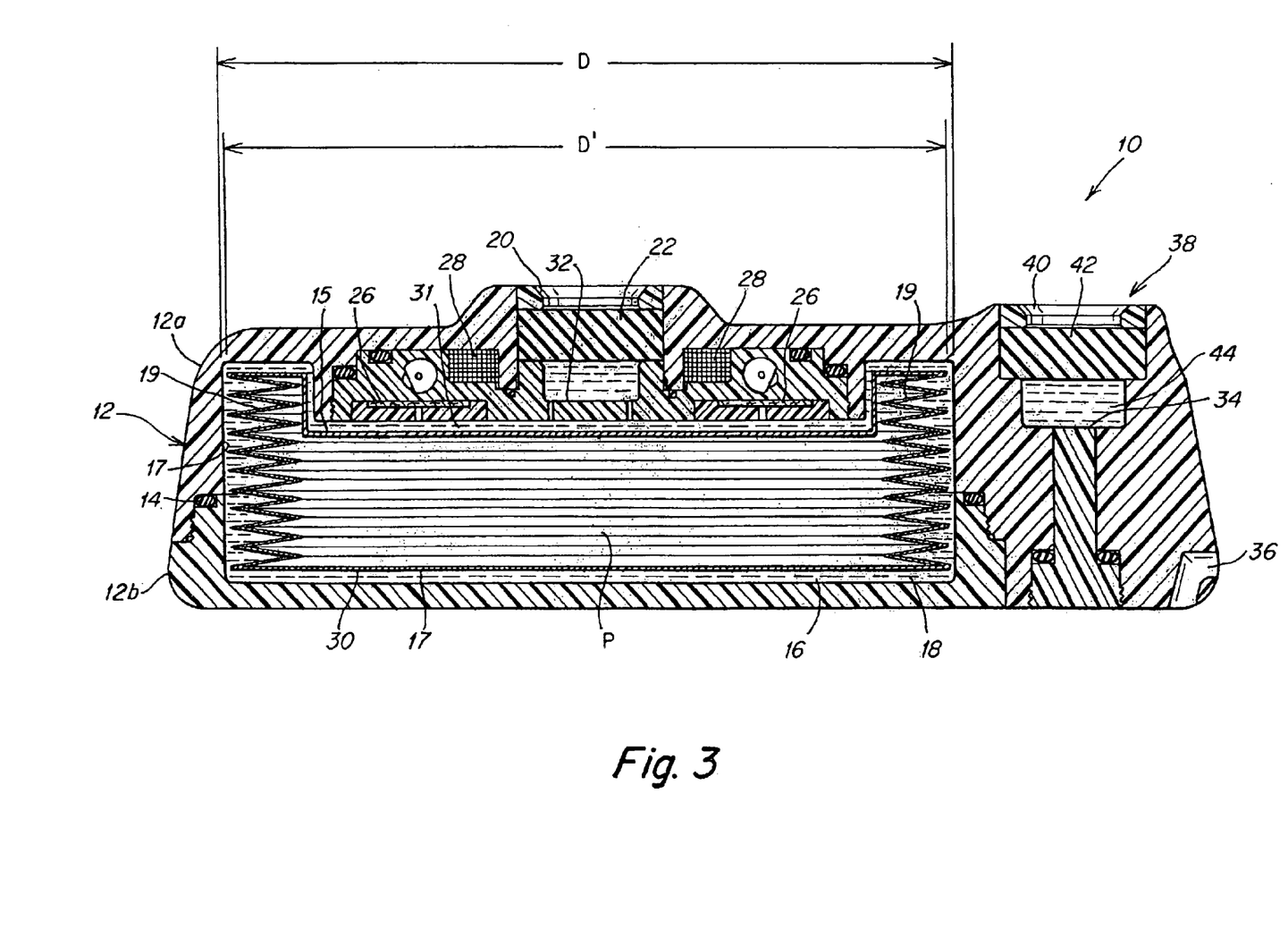
FIG. 3 is a sagittal view of the device of FIG. 1.
Figure 4:
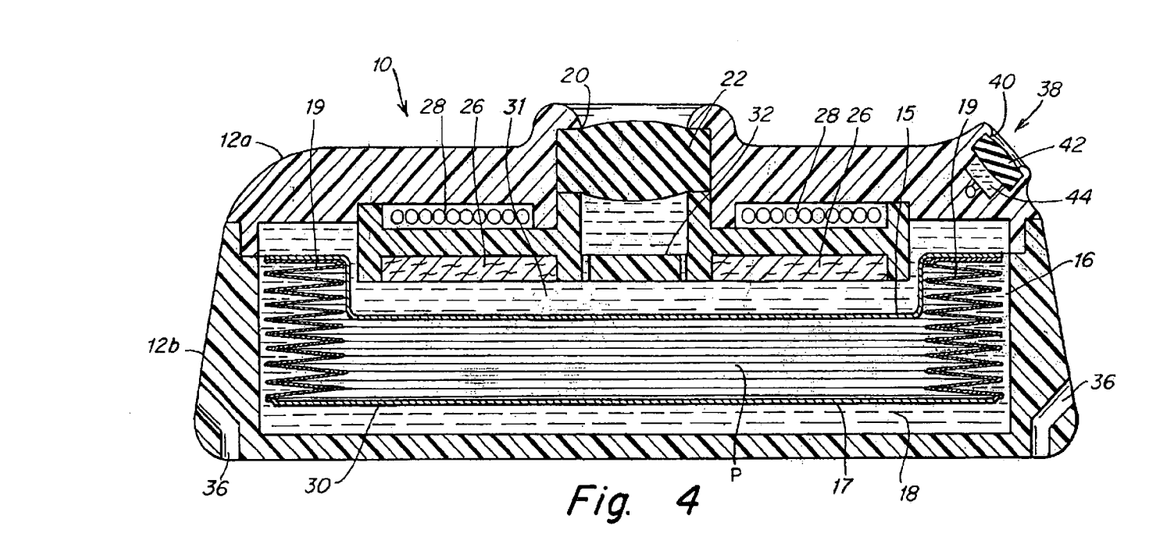
FIG. 4 is a sagittal view of an alternate design of the device, in which the sideport bolus port is located at an angle on a peripheral edge of the device.

The infusion device of the present invention combines several features known in the art in a novel and unobvious way. The device has a relatively low profile, as shown in FIGS. 1, 3 and 4, and is remarkable in several aspects. First, the device can be housed in a lightweight, biologically inert material which need not be hermetically sealed. This is because, unlike most prior art infusion devices, the pressure source in the claimed device, which can be a propellant fluid, a mechanical spring or the like, or a combination of such elements, is contained in a separate enclosed container within the housing of the device, and the infusate, or drug to be administered, is outside the container containing the pressure source.

The container for the pressure source ideally is in the form of a variable volume container, such as a metal bellows or a flexible bag or envelope. However, unlike an expandable balloon bag, the variable volume container has a defined maximum and minimum volume. The infusate is administered to the patient from the device upon expansion of the variable volume container within the interior region of the housing until the variable volume container effectively fills the interior volume of the housing, at which point the infusate is substantially depleted.

The device can also be transcutaneously recharged with infusate without requiring that the device be removed from the patient. Recharging the infusate effectively recharges the pressure source by compressing the variable volume container to its minimum volume and creating pressure which is used to expel the infusate from the device.

The device also includes a separate bolus injection port for introduction of a bolus dose to the patient which bypasses the pressure source-driven delivery of the infusate from the principal reservoir of the device. Pierceable, self-sealing septa through which infusate can be injected into the device are located in the primary and bolus ports of the device for convenient introduction and containment of infusate and bolus injections.

In addition, because the housing can be made of a lightweight material, such as plastic, many features, such as fluid flow channels, compartments, needle stops and suture loops, can be integrated into the housing during its manufacture, which can be accomplished by molding or other low-cost, high-volume manufacturing processes.

Figure 2:
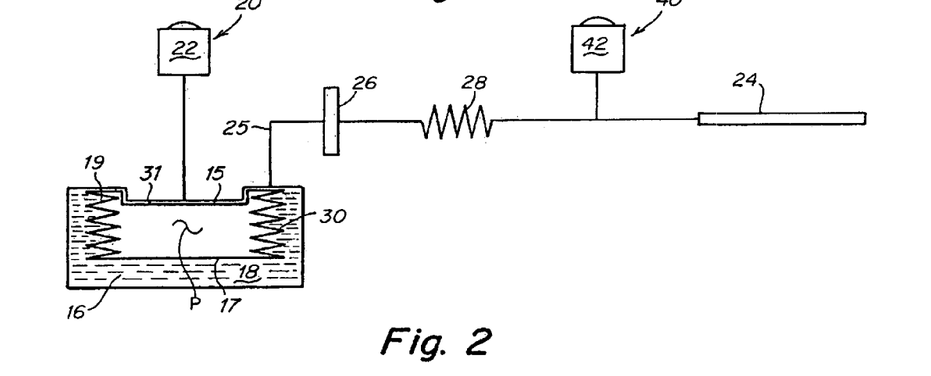
FIG. 2 is a schematic diagram of the device which illustrates its structure and principles of operation.
Figure 2A:
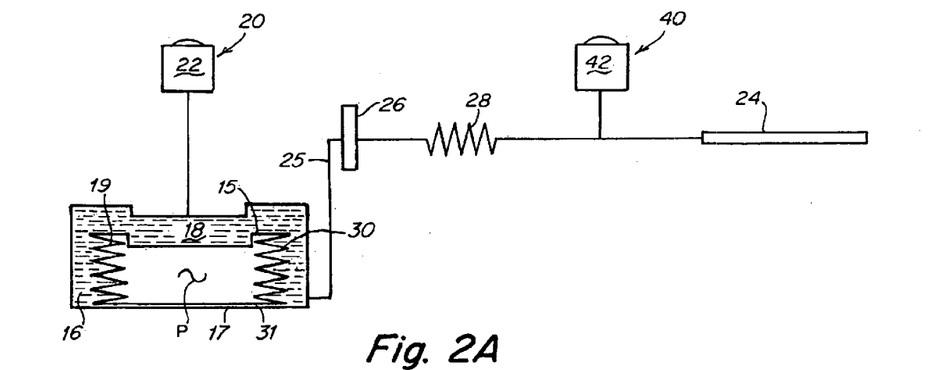
FIG. 2A is a schematic diagram of another embodiment of the device which illustrates its structure and principles of operation.
Figure 5:
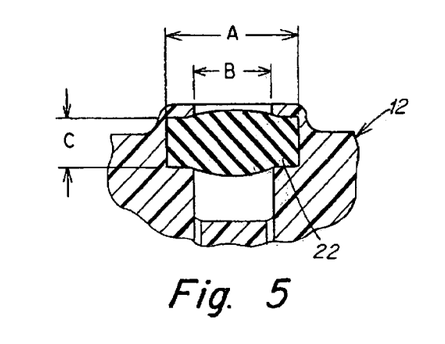
FIG. 5 is a sagittal view of a replaceable septum in a device according to the present invention.
Figures 6A, 6B:
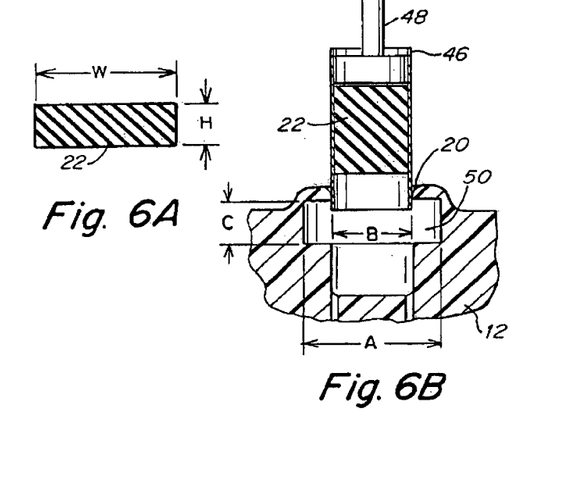
FIGS. 6A–6C illustrate a septum replacement kit and the steps for installing a replacement septum with a septum replacement tool.
Figure 6C:
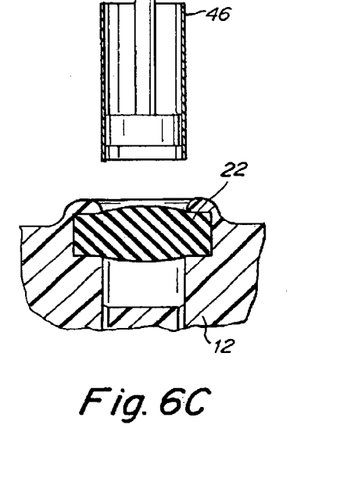
Figures 7A, 7B:
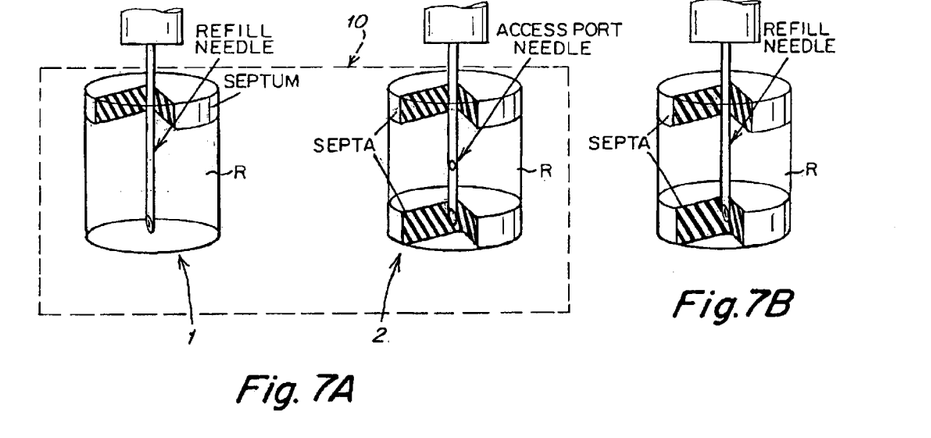
FIGS. 7A–7B illustrate a bolus port safety feature which prevents inadvertent administration of an overdose of drug to the patient through the bolus injection port.

FIG. 1 shows a perspective view of the infusion device 10 according to the invention. FIG. 2 illustrates in schematic form the basic structure and principles of operation of the device. FIG. 2A illustrates in schematic form another embodiment of the basic structure and principles of operation of the device. FIG. 3 is a detailed sectional view of the device of FIG. 1 along a sagittal (vertical longitudinal) axis. FIG. 4 is a sagittal view of an alternate design of the device, in which the side bolus port is located at an angle from a top edge of the device. FIG. 5 is a sagittal view of a replaceable septum for the device. FIGS. 6A–6C illustrate a septum replacement kit and a method of using it to remove a worn septum and replace it with a fresh septum. FIGS. 7A–7B illustrate a bolus safety feature which prevents the inadvertent administration of a principal dose of the drug to be infused through the bolus injection port.

The device 10 is contained within a housing 12 made of a lightweight, durable, and biologically inert material, such as plastic. The housing is conveniently formed of an upper housing 12a and a lower housing 12b, which are joined with an o-ring 14 between them to create a fluid-impermeable seal. The halves of the housing can be joined by, for example, ultrasonic or thermal welding, solvent bonding, or other adhesive-based bonding.

The housing of the device defines an interior region which forms a principal reservoir 16 for the infusate 18, which is typically a drug to be administered over a period of time at a constant low dose to a patient into which the device has been surgically implanted. The infusate is introduced into the principal reservoir via a principal entry port 20, which is sealed with a pierceable, self-sealing septum 22. The infusate is delivered from the principal reservoir to a catheter 24 via exit flow path 25, which may contain at least one of a filter 26 and a flow restrictor 28.

In one preferred embodiment of the invention, the device can include a separate restrictor chamber in the upper half 12a. This separate restrictor chamber permits the use of interchangeable restrictors for establishing different infusate flow rates.

Delivery of the infusate from the principal reservoir is driven by a pressure source P contained within a variable volume enclosed chamber 30, which may be attached to the housing, such as the upper housing 12a or lower housing 12b, but preferably to the upper housing 12a, as detailed more fully below. The pressure source may be a multiple-phase fluid which expands from a liquid phase to a gas phase with increasing temperature, thereby increasing in volume and pushing against the walls of the variable volume container to enlarge it, thereby decreasing the volume of the principal reservoir 16 and expelling the infusate therein from the device. Alternatively, the pressure source can be a mechanical device, such as a spring or other compressible member, or a shape-memory metal alloy. A combination of a propellant fluid and a compressible mechanical member may also be used to obtain a desired infusate delivery rate from the device. The mechanical member may, but need not, exert a constant force throughout its stoke range.

If a propellant fluid is used as the pressure source within the variable volume chamber, it is desirable to have the minimum volume of the chamber be greater than the liquid volume of the propellant fluid, so that the propellant fluid must always exist in the chamber in both liquid and gas phases. In addition, it is desirable to select a propellant fluid which is at a pressure of not less than one atmosphere at ambient temperature, so that at the temperature of use (typically nominal body temperature of the patient) the propellant is at a pressure which is even higher than one atmosphere of pressure. This allows the surgeon to prime and operate the device at ambient temperature in order to verify its performance prior to implantation of the device in the patient, thereby eliminating the need to warm the device and the infusate to body temperature. In addition, such a positive pressure device eliminates the risk that outside air or gases will be drawn into the device during storage of the device.

The inert plastic housing containing the infusate 12 may, but need not, be hermetically sealed. The housing, if made of a moldable or easily formed material, may include, for example, integrally formed needle stops 32, 34 for the primary and bolus injection sites, as well as one or more integrally formed suture loops 36 for passage of anchoring sutures therethrough.

The variable volume chamber 30 is desirably a substantially rigid, gas-impermeable bellows structure, such as one including a top and bottom portions 15 and 17 with serially coupled annular members 19 extending between the top and bottom portions as illustrated in FIGS. 2–4, or other similar rigid-walled or spring-driven structure which occupies a volume which approximates the volume of the principal reservoir 16. Preferred materials for the bellows chamber include metals and plastics. An important feature of the variable volume chamber is its width dimension or diameter D' relative to the diameter D of the housing. It is necessary to have D' be less than D, so that the bellows walls are spaced from the housing a but only by so much as will allow the bellows walls to move freely within the housing. It is desirable to have the bellows walls as close as possible to the housing walls so that maximum displacement of infusate can be achieved by movement of the bellows in the reservoir. However, drag of the bellows walls on the housing walls must be avoided. Thus, it is desirable to have the variable volume chamber centered in the principal reservoir for maximum volume and avoidance of drag and so that the distance D–D' is sufficient to avoid such drag.

Although the device and bellows are illustrated as cylindrical in a preferred embodiment, they may have any convenient shape.

Another important consideration is that the variable volume chamber must not be located so that it obstructs the principal entry port or recharging fluid flow path 20 for infusate when the principal reservoir is empty and the variable volume chamber is at its maximum volume. In a preferred embodiment, the variable volume chamber 30 may be attached to the housing (either upper housing 12a or lower housing 12b) so as to define a fluid flow path 31 between the variable volume chamber and the housing. Alternatively, the chamber 30 and housing 12 may be designed to share a common wall which may be channeled to provide fluid flow paths 31 along the interface between the housing and the chamber 30. In still another alternate embodiment, the bellows may be freely located in the interior region of the housing. In this embodiment, the free bellows is desirably held away from the infusate entry port or recharging fluid flow path 20 by standoffs extending from the bellows or from the infusate entry port.

To ensure as low a profile as possible for the device, it is desirable to construct the housing so that the central portion of one or both of its top and bottom portions, along with corresponding central portions of the top and bottom members of the bellows, is offset or depressed from the nominal plane of the central portions as shown in FIGS. 3 and 4 to form a nested structure. The infusate entry port nests within a recessed central portion of the bellows. Although only the top portions of the housing and bellows are shown as nested in FIGS. 3 and 4, the bottom portions of the housing and bellows could also be nested to further reduce the height of the device. Reductions in the volume of the infusate chamber 30 reduce the amount of infusate that can be administered and increase the frequency with which the chamber 30 must be recharged if drug delivery is to take place over an extended period. However, the pressure source can be selected so as to maximize delivery from a given volume.

The device includes a separate bolus injection port 38, which includes a bolus entry port 40 sealed with a pierceable, self-sealing septum 42, and leading to a bolus reservoir 44, which is in fluid communication with the fluid exit flow path 25 and delivery catheter 24, yet downstream of the filter 26 and flow restrictor 28. Infusate introduced into the bolus port goes directly into the delivery catheter and bypasses the controlled release provided by the action of the pressure source and variable volume chamber on the infusate in the principal reservoir.

Both the principal infusate entry port and the bolus injection port may include sensing devices known in the art which assist the patient and medical staff in locating the devices transdermally so that additional infusate can be introduced to the device without the need for external palpation or surgical removal of the device.

The life of an implantable infusion device such as those described herein is determined in large part by the life of the septum through which the infusate is introduced. Use of a self-sealing material, such as an elastomer, silicone rubber or similar material, for the septum allows the septum to reseal after it has been pierced with a needle. However, even self-sealing materials lose some elasticity after a certain number of uses and must be replaced to ensure that no infusate leaks out of the device.

Septum life, and thus infusion device life, can be optimized by careful selection of the septum material and the dimensions of the septum and the septum chamber in the device. This is shown in FIG. 5. The ratio of the opening dimension of the septum chamber B to the 1 width of the septum chamber A must be such that the entire septum volume can fit within the chamber opening B when the septum is compressed, and such that the chamber width A adequately compresses the septum to provide satisfactory puncture life. The selection of a material for the septum is also an important consideration, as its hardness, as measured by a durometer, must allow for adequate compression of the septum during insertion without comprising puncture life. The height of the septum chamber C must be sufficient to permit the compressed septum to fill the chamber and still be sufficiently axially compressed to achieve the desired puncture life.

A septum replacement kit allows the surgeon to replace a worn septum without surgically removing the device from the patient. Such a kit is illustrated in FIGS. 6A–6C. FIG. 6A shows a septum 22, which is typically in the form of a cylindrical or square plug of height H and width W. The septum is preferably made of a compressible, resilient, penetrable, self-sealing material, such as a rubber or elastomer. FIG. 6B shows the septum lodged in a tubular member 46, which is sized to fit into the entry port 20, having width B, of the infusion device 12. The septum is easily compressed sufficiently to be lodged into the tubular member 46, and a plunger 48 is used to dislodge the septum from the tubular member into the septum chamber 50, which has width A and height C, after it is inserted into the entry port 20, as shown in FIG. 6C. The septum is radially compressed in the chamber to form a penetrable seal. The plunger and tubular member can then be withdrawn.

Removal of a worn septum can be accomplished by inserting a sharp instrument into the septum to cut it into sections that can then be removed from the septum chamber with tweezers or other suitable instrument.

Although the FIGS. illustrate use of the septum replacement kit for replacing the primary septum 22, the kit can also be used to replace the bolus septum 42 in the bolus injection port 40.

In addition, the device may include safety filling devices known in the art to ensure that the patient and medical staff can distinguish between the primary entry port and the bolus injection port so as to avoid inadvertent administration of relatively large doses intended to be administered over time to the patient. When an implanted infusion pump is to be refilled, it may be difficult to determine whether a refill needle is positioned to enter the principal infusate port or the bolus port. Entry of the refill needle into the wrong port for the dose being administered can result in a patient receiving an excessive dose of the drug and therefore must be prevented.

A bolus safety feature in accordance with the present invention is shown and described in connection with FIGS. 7A–7B. FIG. 7A illustrates the two infusate ports in a typical implantable infusion pump 10 according to the invention. The device includes a principal, or center, access port 1 for administration of infusate into the device, and a bolus access port 2 for administration of a bolus injection directly to the patient. The center access port 1 includes a single septum, below which is disposed an infusate reservoir R. To fill the center access port 1, a refill needle having a hole in the tip, as shown in 1, is required.

In contrast, the side bolus access port 2 includes two septa which are spaced apart to define an infusate reservoir R between them. The top septum in the bolus access port 2 secures the delivery needle in place and provides a seal to prevent leakage of the bolus dose once the needle is removed from the bolus port. The bottom septum blocks the opening in the tip of a standard refill needle, shown in 1, should such a needle be inserted into the bolus port. Only a special needle with a side-access opening near the, center of its length, as shown in 1, instead of at or near the tip, as shown in 1, can be used to fill the bolus port.

FIG. 7B shows the result of using a standard delivery needle in the bolus port. The standard delivery needle includes an opening at its tip and no opening in the side. The opening in the tip will be blocked by the lower septum when the needle is inserted into the bolus port, and no infusate will be delivered.

This design of the center and bolus ports in the device of the invention ensures that no bolus dose can be administered inadvertently to a patient, because only a bolus (side-access opening) needle can be used in the bolus port. If a standard delivery needle is accidentally inserted into the bolus port, no infusate can be delivered, and the surgeon can see immediately that the wrong needle is being used, without administering any harmful dose to the patient.

Because certain changes may be made in the above apparatus without departing from the scope of the invention herein disclosed, it is intended that all matter contained in the above description or shown in the accompanying drawings shall be interpreted in an illustrative and not a limiting sense.

What is claimed is:

1. An implantable infusion device, comprising:
   A. a housing having (a) an annular portion with an inner wall defining an interior region having a width dimension D and extending along a central axis, (b) a bottom portion extending from said annular portion and spanning a first end of said interior region, and (c) a top portion extending from said annular portion and spanning a second end of said interior region, said top portion being opposite said bottom portion, wherein said interior region is substantially closed;
   B. a closed fluid-impermeable hollow bellows extending from one of the top and bottom portions of the housing and defining a variable volume region therein and having a plurality of serially coupled annular members extending between top and bottom portions of the bellows, wherein junctions of said coupled annular members are coupled with flexures, said bellows having a maximum outer width dimension D' where D' is less than D, wherein the portion of the housing from which the bellows extends includes a substantially planar annular peripheral portion disposed about a central portion, wherein a pressure source is contained within said variable volume region of said bellows, and wherein said bellows is disposed within said interior region of said housing and rigidly coupled to said portion of the housing from which the bellows extends, whereby said annular members of said bellows are spaced apart from said annular portion of said housing, wherein said housing includes a recharging fluid path from points external to said housing to a region adjacent to said central portion of said portion of said housing from which the bellows extends, and wherein said housing further defines a fluid exit flow path extending from the region between said bellows and said annular portion of said housing to points external to said housing; and C. a separate bolus port in fluid communication with said fluid exit flow path, wherein said bolus port includes a pair of septa disposed therein and spaced apart to define a bolus reservoir therebetween, wherein a delivery needle having an opening near the center of its length is required to deliver infusate to the bolus reservoir.

2. An implantable infusion device, comprising:

A. a housing having (a) an annular portion with an inner wall defining an interior region having a width dimension D and extending along a central axis, (b) a bottom portion extending from said annular portion and spanning a first end of said interior region, and (c) a top portion extending from said annular portion and spanning a second end of said interior region, said top portion being opposite said bottom portion, wherein said interior region is substantially closed;

B. a closed fluid-impermeable hollow bellows disposed about a variable volume region and having a top member, a bottom member, and a plurality of serially coupled annular members extending therebetween, wherein junctions of said coupled annular members are coupled with flexures, said bellows having a maximum outer width dimension D' where D' is less than D, wherein at least one of said top and bottom members includes a substantially planar annular peripheral portion disposed about a central portion, wherein a pressure source is contained within said variable volume region of said bellows, and wherein said bellows is disposed within said interior region of said housing with one of said top and bottom members facing and rigidly coupled to a corresponding portion of said housing, whereby said annular members of said bellows are spaced apart from said annular portion of said housing, wherein said housing includes a recharging fluid flow path from points external to said housing to a region adjacent to said central portion of one of said top and bottom members of said bellows, and wherein the region of coupling between said housing and said bellows defines a fluid dispersal flow path from said region adjacent to said central portion of said coupled member of said bellows to a region between said annular members of said bellows and said annular portion of said housing, and wherein said housing further defines a fluid exit flow path extending from the region between said bellows and said annular portion of said housing to points external to said housing; and C. a separate bolus port in fluid communication with said fluid exit flow path, wherein said bolus port includes a pair of septa disposed therein and spaced apart to define a bolus reservoir therebetween, wherein a delivery needle having an opening near the center of its length is required to deliver infusate to the bolus reservoir.

3. An implantable infusion device, comprising:

A. a housing having (a) an annular portion with an inner wall defining an interior region having a width dimension D and extending along a central axis, (b) a bottom portion extending from said annular portion and spanning a first end of said interior region, and (c) a top portion extending from said annular portion and spanning a second end of said interior region, said top portion being opposite said bottom portion, wherein said interior region is substantially closed; and B. a closed fluid-impermeable hollow bellows extending from one of the top and bottom portions of the housing and defining a variable volume region therein and having a plurality of serially coupled annular members extending between top and bottom portions of the bellows, wherein junctions of said coupled annular members are coupled with flexures, said bellows having a maximum outer width dimension D' where D' is less than D, wherein the portion of the housing from which the bellows extends includes a substantially planar annular peripheral portion disposed about a central portion, wherein a pressure source is contained within said variable volume region of said bellows, and wherein said bellows is disposed within said interior region of said housing and rigidly coupled to said portion of the housing from which the bellows extends, whereby said annular members of said bellows are spaced apart from said annular portion of said housing, wherein said housing includes a recharging fluid flow path from points external to said housing to a region adjacent to said central portion of said portion of said housing from which the bellows extends, and wherein said housing further defines a fluid exit flow path extending from the region between said bellows and said annular portion of said housing to points external to said housing.

4. An implantable infusion device according to claim 3, further comprising a pierceable, self-sealing septum disposed in said recharging fluid flow path.

5. An implantable infusion device according to claim 4, wherein the septum is removable from the housing.

6. An implantable infusion device according to claim 3, wherein a multiple-phase fluid propellant is present in at least one of a liquid phase and a gas phase within said variable volume region of said bellows as a function of ambient temperature, wherein conversion of the propellant from a liquid phase to a gas phase increases the volume displaced by the bellows in the interior region of the housing, thereby exerting a force on a fluid external to said bellows in said housing so as to provide a substantially constant flow rate of said fluid through said fluid exit flow path.

7. An implantable infusion device according to claim 6, wherein said propellant is disposed in said variable volume region of said bellows at a pressure which is not less than atmospheric pressure at ambient temperature.

8. An implantable infusion device according to claim 3, wherein said central portion of said bellows is offset from the plane of said annular peripheral portion of said bellows.

9. An implantable infusion device according to claim 8, wherein a central region of said top or bottom portion of said housing from which the bellows extends is correspondingly offset from the plane of the annular portion of the housing, wherein the offset central region of the housing substantially nests within said offset central portion of said bellows.

10. An implantable infusion device according to claim 3, further comprising a separate bolus port in fluid communication with said fluid exit flow path.

11. An implantable infusion device according to claim 10, further comprising a pair of septa disposed in said bolus port, wherein the septa are spaced apart to define a bolus reservoir therebetween, wherein a delivery needle having an opening near thee center of its length is required to deliver infusate to the bolus reservoir.

12. An implantable infusion device according to claim 3, further comprising a recharging fluid reservoir disposed along said recharging fluid flow path.

13. An implantable infusion device according to claim 3, further comprising at least one of a flow restrictor and a filter disposed along said fluid exit flow path.

14. An implantable infusion device according to claim 3, wherein said housing is made of a gas-impermeable material.

15. An implantable infusion device according to claim 3, wherein the pressure source comprises one or more of the group consisting of multiple-phase fluids, springs, shape memory metal alloys, Belville washers, and compressible materials.

16. An implantable infusion device according to claim 3, wherein said bellows is made of a substantially rigid, gas-impermeable material.

17. An implantable infusion device according to claim 3, wherein said bellows is hermetically sealed.

18. An implantable infusion device according to claim 3, wherein the housing and bellows are cylindrical.

19. An implantable infusion device according to claim 3, wherein the bellows extends from the top portion of the housing.

20. An implantable infusion device according to claim 3, wherein the bellows extends from the bottom portion of the housing.

21. An implantable infusion device, comprising:
A. a housing having (a) an annular portion with an inner wall defining an interior region having a width dimension D and extending along a central axis, (b) a bottom portion extending from said annular portion and spanning a first end of said interior region, and (c) a top portion extending from said annular portion and spanning a second end of said interior region, said top portion being opposite said bottom portion, wherein said interior region is substantially closed; and
B. a closed fluid-impermeable hollow bellows disposed about a variable volume region and having a top member, a bottom member, and a plurality of serially coupled annular members extending therebetween, wherein junctions of said coupled annular members are coupled with flexures, said bellows having a maximum outer width dimension D' where D' is less than D, wherein at least one of said top and bottom members includes a substantially planar annular peripheral portion disposed about a central portion, wherein a pressure source is contained within said variable volume region of said bellows, and wherein said bellows is disposed within said interior region of said housing with one of said top and bottom members facing and rigidly coupled to a corresponding portion of said housing, whereby said annular members of said bellows are spaced apart from said annular portion of said housing, wherein said housing includes a recharging fluid flow path from points external to said housing to a region adjacent to said central portion of one of said top and bottom members of said bellows, and wherein the region of coupling between said housing and said bellows defines a fluid dispersal flow path from said region adjacent to said central portion of said coupled member of said bellows to a region between said annular members of said bellows and said annular portion of said housing, and wherein said housing further defines a fluid exit flow path extending from the region between said bellows and said annular portion of said housing to points external to said housing.

22. An implantable infusion device according to claim 21, further comprising a pierceable, self-sealing septum disposed in said recharging fluid flow path.

23. An implantable infusion device according to claim 22, wherein the septum is removable from the housing.

24. An implantable infusion device according to claim 21, wherein a multiple-phase fluid propellant is present in at least one of a liquid phase and a gas phase within said variable volume region of said bellows as a function of ambient temperature, wherein conversion of the propellant from a liquid phase to a gas phase increases the volume displaced by the bellows in the interior region of the housing, thereby exerting a force on a fluid external to said bellows in said housing so as to provide a substantially constant flow rate of said fluid through said fluid exit flow path.

25. An implantable infusion device according to claim 24, wherein said propellant is disposed in said variable volume region of said bellows at a pressure which is not less than pressure at ambient temperature.

26. An implantable infusion device according to claim 21, wherein said central portion of at least one of the top and bottom members of said bellows is offset from the plane of said annular peripheral portion of said top and bottom members of said bellows.

27. An implantable infusion device according to claim 26, wherein a central region of said portion of said housing coupled to the bellows is correspondingly offset from the plane of the annular portion of the housing, wherein the offset central region of said portion of the housing coupled to the bellows substantially nests within said central portion of the coupled portion of said bellows.

28. An implantable infusion device according to claim 21, further comprising a separate bolus port in fluid communication with said fluid exit flow path.

29. An implantable infusion device according to claim 28, further comprising a pair of septa disposed in said bolus port, wherein the septa are spaced apart to define a bolus reservoir therebetween, wherein a delivery needle having an opening near the center of its length is required to deliver infusate to the bolus reservoir.

30. An implantable infusion device according to claim 21, further comprising a recharging fluid reservoir disposed along said recharging fluid flow path.

31. An implantable infusion device according to claim 21, further including at least one of a flow restrictor and a filter disposed along said fluid exit flow path.

32. An implantable infusion device according to claim 21, wherein said housing is made of a gas-impermeable material.

33. An implantable infusion device according to claim 21, wherein the pressure source comprises one or more of the group consisting of multiple-phase fluids, springs, shape memory metal alloys, Belville washers, and compressible materials.

34. An implantable infusion device according to claim 21, wherein said bellows is made of a substantially rigid, gas-impermeable material.

35. An implantable infusion device according to claim 21, wherein said bellows is hermetically sealed.

36. An implantable infusion device according to claim 21, wherein the bellows is coupled to the top portion of the housing.

37. An implantable infusion device according to claim 21, wherein the bellows is coupled to the bottom portion of the housing.

38. An implantable infusion device according to claim 21, wherein the fluid dispersal flow path includes regions of increased surface contact area in the coupled region between the housing and the bellows.

39. An implantable infusion device according to claim 21, wherein the housing and bellows are cylindrical.

* * * * *